United States Patent
Clerici et al.

[11] Patent Number: 6,096,789
[45] Date of Patent: Aug. 1, 2000

[54] PROCESS FOR THE PREPARATION OF HYDROCARBONS FROM SYNTHESIS GAS

[75] Inventors: Gabriele Clerici, Milan; Vincenzo Piccolo, Paullo, both of Italy; Paul Broutin, Chaponost; Jean-Charles Viltard, Valence, both of France

[73] Assignees: Agip Petroli S.p.A., Rome, Italy; Institut Francais du Petrole, Rueil-Malmaison, France

[21] Appl. No.: 09/295,416

[22] Filed: Apr. 21, 1999

[30] Foreign Application Priority Data

Apr. 23, 1998 [IT] Italy ................... MI98A0865

[51] Int. Cl.⁷ .................................................. C07C 27/00
[52] U.S. Cl. .......................... 518/706; 518/700; 518/715
[58] Field of Search .................... 518/700, 715, 518/706

[56] References Cited

U.S. PATENT DOCUMENTS

| | | |
|---|---|---|
| 2,598,503 | 5/1952 | Burton . |
| 2,680,126 | 6/1954 | Atwell . |
| 3,501,014 | 3/1970 | Fitch et al. ................. 210/512 |
| 5,900,159 | 5/1999 | Engel et al. ................. 210/788 |

*Primary Examiner*—Johann Richter
*Assistant Examiner*—J. Parsa
*Attorney, Agent, or Firm*—Oblon, Spivak, McClelland, Maier & Neustadt, P.C.

[57] ABSTRACT

Process for the production of hydrocarbons from synthesis gas which comprises:

a) feeding to the bottom of a reactor for Fischer-Tropsch reactions a synthesis gas with molar ratios $H_2/CO$ ranging from 1 to 3;

b) discharging from the head of the reactor a hydrocarbon liquid phase containing the catalyst, in suspension;

c) feeding the suspension to at least a first hydrocyclone to obtain a partially separated product containing from 0.5 to 15% by volume of solid particles;

d) feeding the partially separated product to at least a second hydrocyclone to obtain a stream of liquid substantially without solid particles.

6 Claims, 1 Drawing Sheet

PROCESS FOR THE PREPARATION OF HYDROCARBONS FROM SYNTHESIS GAS

The present invention relates to a process for the production of hydrocarbons from synthesis gas.

More specifically, the present invention relates to a process for the production of hydrocarbons, liquid at room temperature and atmospheric pressure, from synthesis gas by means of the Fischer-Tropsch process.

The Fischer-Tropsch technology for preparing hydrocarbons from mixtures of gas based on hydrogen and carbon monoxide, conventionally known as synthesis gas, is known in scientific literature. A summary of the main works on the Fischer-Tropsch synthesis reaction is contained in the Bureau of Mines Bulletin, 544 (1955) entitled "Bibliography of the Fischer-Tropsch Synthesis and Related Processes" H. C. Anderson, J. L. Wiley and A. Newell.

In general the Fischer-Tropsch technology is based on the use of a reactor for chemical reactions which are carried out in triphasic systems where the gas phase bubbles into a suspension of a solid in a liquid. The gas phase consists of synthesis gas, with a molar ratio $H_2/CO$ varying from 1 to 3, the dispersing liquid phase represents the reaction product, i.e. linear hydrocarbons mainly with a high number of carbon atoms, and the solid phase is represented by the catalyst.

The reaction product which is discharged from the reactor consequently consists of a suspension which must be treated to separate the solid (catalyst) from the liquid phase. Whereas the catalyst is recycled to the synthesis reactor, the liquid is subjected to subsequent treatment, for example hydrocracking and/or hydroisomerization treatment, to obtain hydrocarbon fractions of industrial interest.

Published European patent application 609.079 describes a reactor for Fischer-Tropsch reactions consisting of a gas-bubbling column containing a suspension consisting of particles of catalyst suspended in the liquid hydrocarbon. The synthesis gas is fed to the bottom of the reactor whereas the synthesized hydrocarbon is recovered at the head.

To avoid entrainment of catalyst particles, the reactor is equipped with cylindrical filtration devices arranged inside the reactor in the upper part.

Published international patent application WO 97/31693 describes a method for separating a liquid from a suspension of solid particles which comprises, in a first phase, degassing the suspension and, in a second phase, filtrating the suspension through a tangential flow filter. In particular, the suspension comes from a Fischer-Tropsch reactor and consists of synthesized heavy hydrocarbons which entrain the catalyst particles.

Other examples of methods for separating the catalyst contained in the suspension leaving a Fischer-Tropsch reactor are described in published European patent application 592.176, in published international patent application WO 94/16807, in U.K. Patent 2.281.224, in U.S. Pat. Nos. 4,605,678 and 5,324,335 and in German patent 3.245.318.

The Applicants have now found a further process for the production of liquid hydrocarbons by means of the Fischer-Tropsch process which allows the liquid phase to be recovered from the suspension produced, simply and without having to resort to particular filtration systems inside or outside the synthesis reactor.

The present invention therefore relates to a process for the production of hydrocarbons from synthesis gas which comprises:

a) continuously feeding to the bottom of a reactor for Fischer-Tropsch reactions, containing the catalyst dispersed in the liquid phase, a synthesis gas essentially consisting of hydrogen and carbon monoxide in molar ratios $H_2/CO$ ranging from 1 to 3;

b) continuously discharging from the head of the reactor, the Fischer-Tropsch reaction product essentially consisting of a hydrocarbon liquid phase containing the catalyst, in suspension;

c) feeding the suspension to at least a first hydrocyclone to obtain a concentrated bottom product, recycled to the synthesis reactor, and a partially separated product containing from 0.5 to 15% by volume of solid particles;

d) feeding the partially separated product to at least a second hydrocyclone to obtain a second concentrated bottom product, recycled to the reactor, and a stream of liquid substantially without solid particles.

According to the process of the present invention, the reactor for Fischer-Tropsch-type reactions is a bubble reactor consisting of a container, generally vertical, for example a column, inside of which chemical reactions are activated, which take place in triphasic systems where a gas phase bubbles into a suspension of a solid in a liquid. In the present case, the gas phase consists of synthesis gas, with a molar ratio $H_2/CO$ varying from 1 to 3, the dispersing liquid phase represents the reaction product, i.e. linear hydrocarbons mainly with a high number of carbon atoms, and the solid phase is represented by the catalyst.

The synthesis gas preferably comes from steam-reforming or from the partial oxidation of natural gas, on the basis of the reactions described in U.S. Pat. No. 5,645,613. Alternatively, the synthesis gas can come from other production techniques such as, for example, from "autothermal reforming" or from the gassification of carbon with water vapour at a high temperature, as described in "Catalysis Science and Technology", Vol. 1, Springer-Verlag, New York, 1981.

Two phases are substantially produced from the Fischer-Tropsch reaction, a lighter one, in vapour phase, essentially consisting of light hydrocarbons, water vapour, inert products, etc., which is discharged at the head together with the non-reacted gas, the other heavier phase essentially consisting of paraffinic waxes, liquid at the reaction temperature, comprising mixtures of saturated, linear hydrocarbons with a high number of carbon atoms. These hydrocarbon mixtures generally have a boiling point which exceeds 150° C.

The Fischer-Tropsch reaction is carried out at temperatures ranging from 150 to 400° C., preferably from 200 to 300° C., maintaining a pressure inside the reactor of 0.5 to 20 MPa. More specific details on the Fischer-Tropsch reaction are available in "Catalysis Science and Technology" mentioned above.

Finally, the catalyst is present inside the reactor, suspended in the hydrocarbon liquid phase.

Any catalyst capable of being active in the Fischer-Tropsch reaction can be used in the process of the present invention. The preferred catalyst is based on cobalt, in metal form or in the form of oxide or (in)organic salt, dispersed on a solid carrier consisting of at least one oxide selected from one or more of the following elements: Si, Ti, Al, Zn, Mg. Preferred carriers are silica, alumina or titania.

In the catalyst, the cobalt is present in quantities ranging from 1 to 50% by weight, generally from 5 to 35%, with respect to the total weight.

The catalyst used in the process of the present invention can also contain additional elements. For example, it can comprise, with respect to the total, from 0.05 to 5% by weight, preferably from 0.1 to 3%, of ruthenium and from 0.05 to 5% by weight, preferably from 0.1 to 3% of at least a third element selected from those belonging to Group IIIB. Catalysts of this type are known in literature and described, together with their preparation, in published European patent application 756.895.

Further examples of catalysts are again based on cobalt but containing tantalum as promoter element in quantities of 0.05–5% by weight with respect to the total, preferably 0.1–3%. These catalysts are prepared by first depositing a cobalt salt on the inert carrier (silica or alumina), for example by means of the dry impregnation technique, followed by a calcination step and, optionally, a reduction and passivation step of the calcinated product.

A derivative of tantalum (particularly tantalum alcoholates) is deposited on the catalytic precursor thus obtained, preferably with the wet impregnation technique followed by calcination and, optionally, reduction and passivation.

The catalyst, whatever its chemical composition may be, is used in the form of a finely subdivided powder with an average diameter of the granules ranging from 10 to 700 micrometers.

The Fischer-Tropsch reaction product, which comprises both the hydrocarbon phase and the catalyst, is continuously discharged from the head of the synthesis reactor. It is a suspension in which the concentration of the solid phase generally ranges from 20 to 40% by volume.

The suspension can be degassed, operating both inside and outside the reactor. For example the suspension can be degassed by feeding it to a stirred vertical container, and the gases released from the liquid phase are sent outside and joined to the vapour phase discharged from the head of the reactor.

The suspension, optionally degassed, is fed to a first hydrocyclone (or hydrocyclone battery) for a first quantitative separation. The hydrocyclone is a means of solid-liquid separation in which the separation takes place by centrifugation and the centrifugal movement is guaranteed by a rotating movement obtained by keeping the device steady and tangentially feeding the suspension. A detailed description of the hydrocyclone is available in "Ullmann's Encyclopedia of Industrial Chemistry", Fifth Edition, 1988, Volume B2 or in "Hydrocyclones", L. Svarovsky Holt, Rinehart and Winston, 1984.

During the rotating movement, the particles are pushed against the walls of the device and, losing energy, precipitate and concentrate on the bottom of the hydrocyclone. Two streams can therefore be recovered from the hydrocyclone, one, from the bottom, consisting of a concentrated suspension, the other, from the head, consisting of a diluted suspension containing from 0.5 to 15% by volume approximately of solid particles, generally from 2 to 7%.

The concentrated suspension is recycled to the synthesis reactor whereas the more dilute suspension is fed to a second hydrocyclone (or hydrocyclone battery) from which a stream substantially without solid particles (less than 0.5% by volume) is recovered, which is fed to the subsequent operating phases required by the Fischer-Tropsch process.

Another stream, more concentrated with respect to the one fed, is recovered from the bottom of the second hydrocyclone and can be recycled to the synthesis reactor.

The process for the production of hydrocarbons from synthesis gas of the present invention can be better understood by referring to the process schemes of the enclosed figures which represent two illustrative but non-limiting embodiments.

In particular, the scheme of FIG. 1 refers to a process in which the circulation of the suspension between reactor and first hydrocyclone is guaranteed by the so-called "gas-lift" effect which arises when operating with suspensions having, as in this case, different densities, taking advantage of the hydrostatic liquid seal which is formed between the bubbled suspension (inside the reactor), with a lower density, and the degassed suspension (inside the hydrocyclone) with a higher density. Information on the "gas lift" effect is available in "Industrial and Engineering Chemical Research", 1988, 37, 41–48, 240–246, or in "Chemical Engineering Science", 1977, 52, 2527–2540.

The scheme of FIG. 2, on the other hand, refers to a process in which the reactor and first hydrocyclone are substantially at the same pressure and the circulation of the suspension between the two devices is guaranteed by a hydraulic pump.

BRIEF DESCRIPTION OF THE DRAWING

With reference to the figures, the process schemes comprise: a Fischer-Tropsch reactor (FT), a degasser (D), two pumps (P1) and (P2), two hydrocyclones (IC1) and (IC2).

The functioning of the present process is evident from the enclosed scheme and previous description. The synthesis gases (1) are fed to the base of the reactor (FT), of the bubble-type. The suspension (2), consisting of the liquid phase and catalyst is discharged from the head of the reactor and is fed to the container (D) for degassing. The gases (3) released from the container (D) are joined to the vapour phase (4) leaving the reactor (FT) which is treated, in operating units not illustrated, for the recovery of the entrained hydrocarbons.

The suspension, optionally removed by the pump (P1), is fed, with (5), to the first hydrocyclone (IC1) from which two streams are recovered. One, concentrated (6), is recycled to the reactor (FT), the other, partially separated (7), is removed by the pump (P2) and fed, with (8), to the second hydrocyclone (IC2).

A liquid stream (9), substantially without particles, is discharged from the head of (IC2), whereas a second concentrated stream (10) is discharged from the bottom and recycled to the reactor (FT).

Two illustrative but non-limiting examples are provided for a better understanding of the present invention and for its embodiment.

EXAMPLE 1

Figure 1:
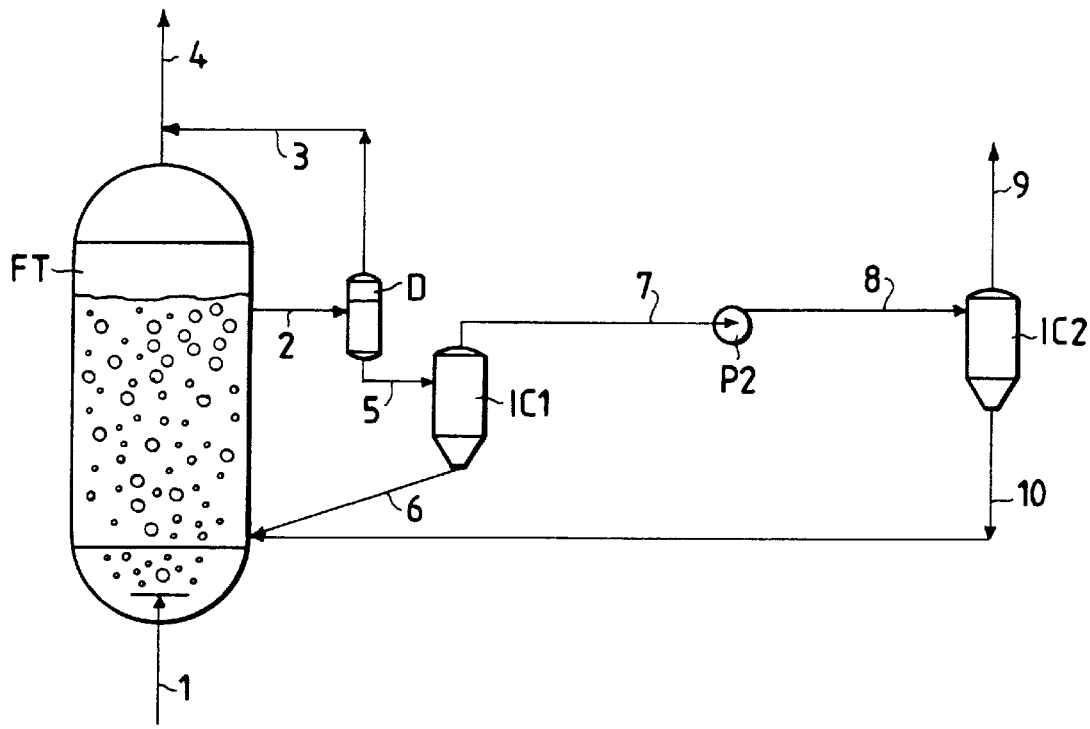

A catalyst with a particle size ranging from 20 to 150 $\mu$m, consisting of an alumina carrier having a surface area of 175 $m^2$/g on which 14% by weight of cobalt and 0.5% by weight of tantalum are distributed, is charged into a reactor/column for Fischer-Tropsch reactions (FT) inserted in the process of FIG. 1.

After activating the reaction, a stream of synthesis gas with a molar ratio $H_2/Co=2$, is fed to the bottom of the reactor, in steady condition. The reaction is carried out at 225° C. and a pressure of 3 MPa.

1 $m^3$/h of a hydrocarbon suspension containing 28% by volume of catalyst is removed continuously from the reactor. After degassing in (D) the suspension is fed to the first hydrocyclone (IC1) from whose bottom about 0.83 $m^3$/h of a suspension concentrated at 32% by weight is recovered and recycled to the reactor (FT), whereas about 0.12 $m^3$/h of a partially separated suspension containing 6.5% by volume of catalyst are recovered from the head.

The partially separated suspension is fed to the second hydrocyclone (IC2) which supplies, at the head, 0.1 m³/h of a clarified liquid stream (with a concentration of catalyst of less than 0.5% by volume) and, at the bottom, about 0.02 m³/h of a thickened suspension containing 32% by volume of solid which is recycled to the synthesis.

EXAMPLE 2

Figure 2:
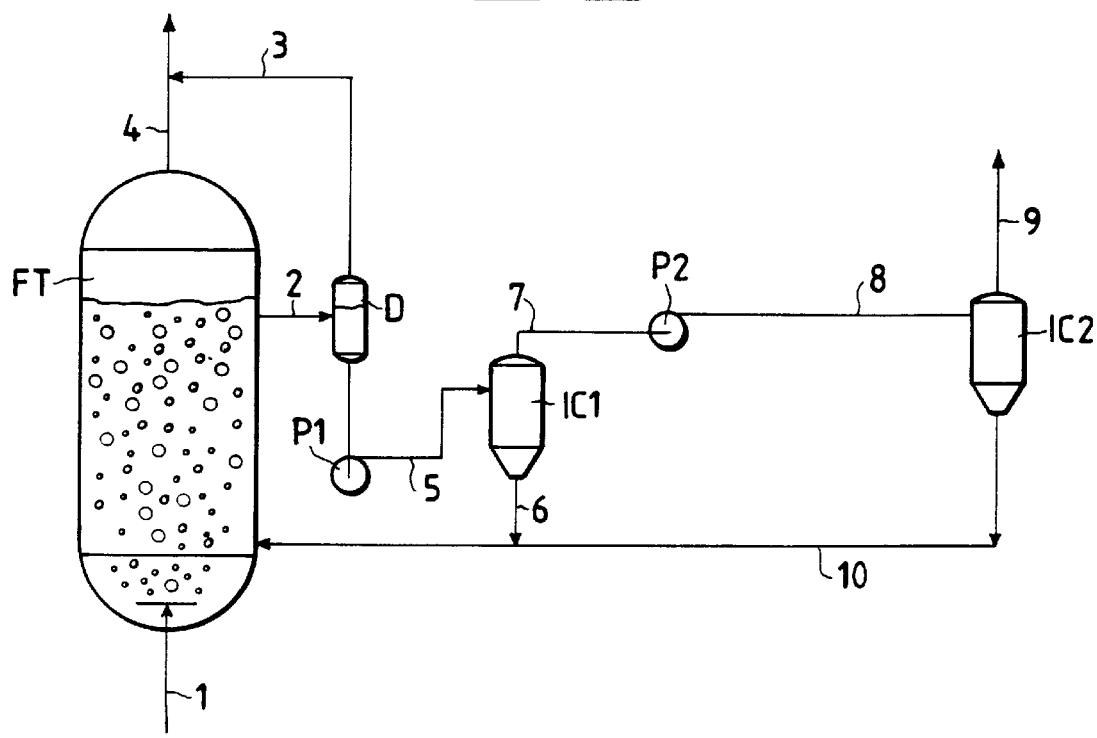

The same procedure is carried out as in example 1, except that reference is made to the scheme of FIG. 2.

1 m³/h of suspension at 25% by volume of solid is removed continuously from the reactor (FT) and, after degassing, is sent by pump (P1) to the first hydrocyclone. 0.88 m³/h of suspension concentrated at 28% by volume of solid, are recovered and recycled to the reactor (FT), together with 0.1 m³/h of partially separated suspension containing 5% by volume of catalyst.

The partially separated suspension is fed to the second hydrocyclone (IC2) which supplies, at the head, 0.08 m³/h of a clarified liquid stream (with a concentration of catalyst of less than 0.5% by volume) and, at the bottom, 0.02 m³/h of a suspension containing approximately 23% by volume of solid, which is recycled to the synthesis.

What is claimed is:

1. A process for the production of hydrocarbons from synthesis gas which comprises:
   a) continuously feeding to the bottom of a reactor for Fischer-Tropsch reactions, containing the catalyst dispersed in the liquid phase, a synthesis gas essentially consisting of hydrogen and carbon monoxide in molar ratios $H_2/CO$ ranging from 1 to 3;
   b) continuously discharging from the head of the reactor, the Fischer-Tropsch reaction product essentially consisting of a hydrocarbon liquid phase containing the catalyst, in suspension;
   c) feeding the suspension to at least a first hydrocyclone to obtain a concentrated bottom product, recycled to the synthesis reactor, and a partially separated product containing from 0.5 to 15% by volume of solid particles;
   d) feeding the partially separated product to at least a second hydrocyclone to obtain a second concentrated bottom product, recycled at least partially to the first hydrocyclone, and a stream of liquid substantially without solid particles.

2. The process according to claim 1, wherein the reactor for Fischer-Tropsch reactions is a vertical bubble reactor.

3. The process according to claim 1 or 2, wherein the Fischer-Tropsch reaction product in liquid phase essentially consists of paraffinic waxes which have a boiling point higher than 150° C.

4. The process according to claims 1 or 2, wherein the Fischer-Tropsch reaction is carried out at temperatures ranging from 150 to 400° C. and a pressure ranging from 0.5 to 20 MPa.

5. The process according to claims 1 or 2, wherein the suspension produced in the Fischer-Tropsch reactor is subjected to degassing.

6. The process according to claims 1 or 2, wherein the suspension after the first filtration has a concentration of solid ranging from 2 to 7% by weight.

* * * * *